United States Patent [19]

Cercone

[11] Patent Number: 5,744,150
[45] Date of Patent: Apr. 28, 1998

[54] SOFTENED ANTIMICROBIAL SPONGE MATERIAL WITH COLOR CHANGE INDICATION OF ANTIMICROBIAL ACTIVITY

[75] Inventor: Ronald J. Cercone, East Lyme, Conn.

[73] Assignee: Xomed Surgical Products, Inc., Jacksonville, Fla.

[21] Appl. No.: 787,018

[22] Filed: Jan. 29, 1997

[51] Int. Cl.$^6$ .......................... A01N 25/34; A61F 13/02; C08J 6/00; C08F 8/00
[52] U.S. Cl. .......................... 424/404; 424/405; 424/78.6; 424/486; 424/445; 424/431; 424/423; 424/78.26; 424/667; 523/122; 521/82; 525/61
[58] Field of Search .......................... 424/405, 78.6, 424/404, 486, 445, 431, 423, 78.26, 667; 523/122; 521/82; 525/61

[56] References Cited

U.S. PATENT DOCUMENTS

| | | | |
|---|---|---|---|
| 2,375,963 | 5/1945 | Thomas | 18/48 |
| 3,724,465 | 4/1973 | Duchane | 604/363 |
| 3,911,107 | 10/1975 | Krezanoski | 424/667 |
| 4,031,209 | 6/1977 | Krezanoski | 424/672 |
| 4,125,602 | 11/1978 | Atasoy et al. | 525/358 |
| 4,214,059 | 7/1980 | Hofer | 424/78.25 |
| 5,071,648 | 12/1991 | Rosenblatt | 424/78.06 |
| 5,180,061 | 1/1993 | Khan et al. | 206/570 |
| 5,252,340 | 10/1993 | Honeycutt | 424/489 |
| 5,302,385 | 4/1994 | Khan et al. | 424/486 |

*Primary Examiner*—Marian C. Knode
*Assistant Examiner*—Ali Salimi

[57] ABSTRACT

A method for producing an improved antimicrobial material thereby producing a soft, dry, iodine/acetalized polyvinyl alcohol complex sponge material having a pleasing yellow-gold coloration which self-indicates activation of the antimicrobial elements in the complex.

12 Claims, No Drawings

SOFTENED ANTIMICROBIAL SPONGE MATERIAL WITH COLOR CHANGE INDICATION OF ANTIMICROBIAL ACTIVITY

BACKGROUND OF THE INVENTION

1. Field of the Invention

The present invention relates to a method for treating an iodine/polyvinyl acetal complex sponge material to produce an antimicrobial sponge material having a soft texture and being color indicative of antimicrobial activity.

2. Discussion of the Related Art

Numerous potential pathogens may be present on the skin and exposed tissue. It is desirable for the growth of disease-producing microorganisms to be inhibited and preferably for these microorganisms to be destroyed to control patient infection and encourage wound healing. As a result, the application to the skin or tissue of topical microbial active agents has become a standard part of aseptic technique for wound care.

Iodine is an outstanding microbicide, with an extraordinary range of action. Part of its mode of action is that it is able to penetrate the cell walls of microorganisms rapidly, and block certain essential hydrogen-bonding in amino acids. Also, iodine has a powerful, oxidizing effect on S—H, —S—S— groups, which are essential factors in protein production. Iodine is effective against a wide range of microorganisms, including bacteria, tubercle bacilli (Mycobacteria), fungi, protozoa, lipid and medium viruses, as well as non-lipid and small viruses. Iodine is designated as an intermediate germicide only because spores are not readily killed by the application of weak concentrations of iodine. However, iodine has the greatest degerming efficiency compared to other halogens, such as chlorine and bromine, since iodine is deactivated by proteins at least three times slower than chlorine and four times slower than bromine. Therefore, under normal conditions of use, in the presence of large amounts of dissolved proteins, as are present in blood, serum or sputum, iodine is less likely to be rendered ineffective. Iodine has the additional advantage that its disinfecting properties are independent of the pH value of its environment. Therefore, unlike chlorine, iodine is not rendered ineffective in an acid pH environment. Iodine is also not deactivated quickly in an alkaline pH environment.

Low concentrations of iodine react relatively slowly with proteins in general and therefore iodine remains available to react with bacteria for which iodine generally has a greater affinity. Iodine is, in this way, likely to exhibit its unique advantageous selectivity towards microorganisms while maintaining a very low level of cytotoxicity to the host cells. However, because of iodine's physical and inherent chemical properties; its use as an antiseptic, broad spectrum antimicrobial had been limited because delivery methods allowed for the liberation of quantities of free iodine in excessive amounts potentially toxic to living cells.

This problem was substantially overcome with the development of a polyvinyl acetal sponge capable of releasing controlled amounts of iodine as disclosed in U.S. Pat. No. 5,071,648 issued to Solomon Rosenblatt on Dec. 10, 1991 and which is assigned to the assignee of the present invention. The polymeric antimicrobial containing acetalized polyvinyl alcohol sponge material prepared in U.S. Pat. No. 5,071,648 released controlled amounts of iodine sufficient to kill germ cells with minimal toxicity to surrounding tissue. This sponge included insoluble antimicrobial polymeric iodophors as complexes of acetalized polyvinyl alcohol and iodine or borate or combinations thereof. A complex of acetalized polyvinyl alcohol (polyvinyl acetal) and iodine was thus produced having a low solubility such that iodine was released in a sustained and controlled manner and in an amount capable to kill germs but not capable to cause damage to living tissue. This iodine/polyvinyl acetal complex was generally unacceptable as a wound dressing since the resulting sponge product is a black, dry, rigid material. This material was unsuitable for use in applications such as wound care dressings because its rigidity resulted in a lack of flexibility and an inability to conform to appropriate body curvatures. Additionally, an aesthetic, cosmetic objection was raised to the black color of the resultant product.

OBJECTS AND SUMMARY OF THE INVENTION

Accordingly, it is a primary object of the present invention to produce a flexible, antimicrobial sponge having the ability to be contoured to conform to appropriate body curvatures.

It is a further object of the present invention to produce an antimicrobial sponge having a softer outer texture than the dry, rigid sponge materials produced using the methods taught in the prior art.

It is another object of the present invention to produce an antimicrobial sponge having a visually pleasing color.

It is a further object of the present invention to produce a soft, dry yellow-gold antimicrobial polyvinyl acetal sponge material displaying a color change as an indication of activation of an iodine/polyvinyl acetal complex.

In the method of the present invention, a polyol, such as alkylene glycol, preferably triethylene glycol, is used to impregnate or coat a iodine/polyvinyl acetal complex containing sponges in order to accelerate the formation of iodates and iodine dioxide on the surface of the sponges and imparting a gold color to the surface of the sponges. Since the polyols used in the present invention act as humectants, the polyol treated sponges, upon exposure to water or moisture, in the ambient air retain water thereby softening the sponges and preventing increased rigidity normally associated with drying of the sponges.

In the preferred embodiment of the method of the present invention, a sponge containing an iodine/polyvinyl acetal complex, is soaked in an aqueous bath containing triethylene glycol, preferably in an amount ranging between 20% to 70% by volume. This soaking procedure permanently softens the sponge and imparts a golden color to the surface of the sponge. Any excess glycol is removed from the sponge by centrifugal extraction.

In a second embodiment, an aqueous spray or roller containing an alkylene glycol is applied to the surface of the iodine/polyvinyl acetal complex sponge to soften the sponge and impart a golden color onto the outer surface of the sponge.

The method of the present invention may be used to soften any polyvinyl acetal sponge material, even in the absense of iodine in the sponge.

The antimicrobial sponge of the present invention, when packaged dry, retains its golden color until used. At the moment of contact with moisture from an aqueous solution such as blood, serum, plasma or another fluid, the sponge material reverts to the active black color thereby producing a visual indication of antimicrobial activity. The black color disappears as the iodine component of the iodine/polyvinyl acetal complex is depleted through its reaction with a protein containing compound such as bacteria and the like. Complete iodine depletion in the sponge is indicated by a return to the white color of the polyvinyl acetal material, thereby providing a second visual indication to the user that antimicrobial capacity has been depleted. The sponge material of the present invention can be used to produce any number of bandages or cosmetic products such as earring disks, adhesive "zit" spots, pads or any number of other products.

The foregoing and additional objects, features and advantages of the present invention will become apparent to those of skill in the art from the following detailed description of the preferred embodiment.

DETAILED DESCRIPTION OF THE PREFERRED EMBODIMENTS

Well known in the art are various polyvinyl alcohol (PVA) polymers and derivatives having desirable physical and mechanical properties. These polymers have been synthesized and subsequently complexed with iodine for use in the present invention. It is well known that formalized, preferably medium molecular weight, fully hydrolyzed polyvinyl alcohol in the form of cellular materials, or formalized or unformalized sheets, gels or coatings of PVA complexed with iodine, produce relatively insoluble iodophors with excellent antimicrobial properties and controlled, sustained release properties over an extended time. One example of a formalized PVA polymer is an open celled foam, as described in U.S. Pat. No. 4,098,728. This foam or open celled sponge was subsequently complexed with iodine to illustrate the characteristics of formalized PVA foam iodine complexes. Any other formalized PVA foam such as those previously described, for example, in U.S. Pat. Nos. 2,609,347, 3,663,470 and 3,737,398, may be similarly complexed with iodine. Furthermore, formalized and unformalized PVA gels and coatings, complexed with iodine either pre- or post-formation, are also useful in the present invention. Thus in the following description of the invention and in the claims the term "PVA/I complex" is herein defined to include formalized, partially formalized and unformalized PVA complexed with iodine as produced or disclosed in U.S. Pat. Nos. 2,609,347, 3,663,470, 3,737,398, 4,098,728 and 5,071,648, the disclosures of these patents are incorporated herein by reference.

The iodine in these complexes may be derived preferably from potassium iodide solubilized iodine. Polyvinylpyrrolidone (PVP)/Iodine complexes are also sources of iodine for the PVA/I complex, as the PVA/I complex is more stable and reacts with the iodine from the PVP. Sublimed iodine having vapor reactive with the PVA, chloroform solutions, and tinctures, are examples of other sources of iodine for the PVA/I complex.

In the method of the first embodiment, a PVA/I complex, preferably an iodine/polyvinyl acetal (partially formalized PVA) complex sponge, is produced in accordance with the teachings of U.S. Pat. No. 5,071,648 to Solomon Rosenblatt on Dec. 10, 1991. The polyvinyl acetal material has a uniformly controlled pore size throughout its volume, is fast wicking and has a high liquid holding capacity; the material is marketed under the trademark MEROCEL and is specifically described in U.S. Pat. No. 4,098,728, issued Jul. 4, 1978.

The present invention employs a method to treat the black, antimicrobial PVA/I complex sponge material, preferably as produced and described in U.S. Pat. No. 5,071,648, by immersing the PVA/I complex sponge in a polyol such as an alkylene glycol or by spraying the surface of the PVA/I complex sponge with a polyol. This improved method produces a soft, dry sponge product having a yellow-gold coloration produced by the interaction of the iodine and the alkylene glycol.

When the surface of the alkylene glycol treated PVA/I complex sponge material comes into contact with moisture from blood, serum, plasma or other biological fluids the sponge material reverts back to an active black color. This black color disappears as the iodine component of the PVA/I complex is depleted by reaction with protein containing compounds and microbial source such as bacteria or the like. A visual indication of depletion of the iodine in the PVA/I complex occurs as the PVA material turns to a white color.

In the method of the present invention, a soft, yellow-gold colored sponge material is produced having the same antimicrobial properties and slow release characteristics as the PVA/I complex of the patents discussed above. The new sponge material remains soft by absorbing sufficient moisture from the atmosphere to soften the complex. The applicant has discovered that polyols, preferably alkylene glycols, such as triethylene glycol, and other equivalent glycols, accelerate the formation of iodates and iodine dioxide on the surface of the PVA/I complex. These polyols act as humectants, holding water, thereby softening the sponge complex and preventing drying and act as plasticizers preventing subsequent rigidification of the sponge.

The plasticizer incorporated into the composition of the present invention may be any biocompatible plasticizer or mixture thereof suitable as humectants and useful for plasticizing the PVA/I complex derived substances. Among suitable plasticizers for use in accordance with the present invention, a water-soluble hygroscopic polyols. Among the specific water-soluble hygroscopic polyhydroxy compounds which can be used herein with generally good results are polyols including alkylene glycols useful in the present invention as humectants and plasticizers are $C_2$–$C_{12}$ alkylene glygols and triols including but not limited to: ethylene glycol, propylene glycol, diethylene glycol, triethylene glycol, dipropylene glycol, tripropylene glycol, neopentyl glycol, glycerin, trimethylol propane, trimethylol ethane and the like, and mixtures thereof Triethylene glycol is especially preferred for use in the present invention.

A preferred method of coating an article that is substantially rigid, e.g., a formed bandage, etc., involves spray coating or rolling the article with an aqueous solution of the polyol containing coating, preferably with an air brush or with a fluidized bed coating technique. The aqueous solution can be prepared with any order of mixing ingredients. In other words, the polyol can all be mixed with water to form a solution of appropriate concentration. Preferably, the alkylene glycol is added to water at a level of about 1% to about 99% by volume of polyol of the resulting solution, more preferably about 10% to about 80% by volume of the resulting solution, and most preferably from about 20% to about 70% by volume of the resulting solution.

The spray coating of the coating solution is generally carried out at a temperature of about 30° C. to about 50° C., preferably at about 40° C. As noted above, spraying is preferably carried out with an air brush such as Badger Model 150 available from Badger Air Brush Company, Franklin Park, Ill. Alternatively, a fluidized bed coating technique can be employed, such as fluidized bed coating attained using a Versa Glatt GPCG-1 fluidized bed coater available from Glatt Air Techniques, Ramsay, N.J. Of the various types of fluidized bed coating, top spraying of fluidized articles has been found suitable. Generally, the coating is sprayed to have a color indicating surface thickness upon each article of about 0.01 to about 0.10 mm after drying.

In the method of the preferred embodiment, a PVA/I complex sponge is soaked in a bath of a polyol preferably an aqueous solution containing triethylene glycol. The triethylene glycol solution is preferably 20% to 70% by volume triethylene glycol. This soaking step permanently softens the PVA/I complex sponge material. Excess polyol is then removed from the sponge material by centrifugal extraction.

In a second embodiment of the present invention, only the surface is sprayed with the polyol solution described above. When only the surface has been sprayed or rolled, the surface is softened and the interior of the sponge remains rigid. Such foam materials having a soft outer surface and a rigid interior are useful in the production of specifically shaped sponge materials necessarily having a requirement of rigidity such as splint-type products.

Use of a suitable polyol, particularly triethylene glycol or other alkylene glycols, may be employed to soften any polyvinyl alcohol based sponge material, with or without the presence of an iodine complex. However, the beneficial softening of the iodine PVA complex is especially well suited to use in medical bandages and packings since the combination of antimicrobial activity and a soft conforming sponge provides a uniquely effective therapeutic effect.

The softened iodine/PVA complex sponge is packaged in a dried state and retains its golden color until used, whereupon, at the moment of contact with an aqueous solution such as blood, serum, plasma, sputum or other bodily fluids, the material reverts to the original active black color and thereby provides a visual indication for the medical professional or other user that the antimicrobial benefits of the product have been activated. Over time, the black color disappears as the iodine component of the complex is depleted by reaction with protein containing compounds such as blood or bacteria. Complete iodine depletion is indicated by a return to a white color for the PVA sponge material. This provides a second visual indication to the health care professional or the user that the antimicrobial capacity of the sponge complex has been depleted.

The softened golden iodine/PVA complex sponge material may be employed in a variety of products, such as: small bandages and antimicrobial cosmetic products, earring disks, adhesive "zit" spots, pads, tampons, panty liners, vaginal pads, perineal pads, surgical pads, surgical drapes, baby diapers, surgical instrument covers, surgical instrument protectors, surgical wipes, surgical instrument cleaners, adult incontinence pads, adult incontinence diapers, sanitizing or cleaning pads for household or industrial use, strip type bandages, burn covers, wound covers, wound dressings, burn dressings, foot odor stoppers, shoe insole liners, sneaker liners, acne pads, fruit wrappers, box or crate liners, woman's dress underarm shields, men's suit underarm shields, military field bandages, decubitus ulcer dressings, decubitus ulcer cleaning wipes, wound cleaning wipes, debridement wipes, contraceptive sponges, toilet seat covers, hand sanitizing wipes, vaginal anti-candida fungus pads, patient bed pads, broadloom and carpet liners (to control buildup of bacteria and fungi), colostomy site covers, operation site covers, round catheter covers, drainage site covers, artero-venus shunt dressings and covers, shower floor mats, locker room runners and mats, continuous bandage strips, ear wick devices, underliners for disposable baby blankets or wraps, sterilizing wipes, ear cleaning swabs, naval (umbilicus) cleaning swabs, medicated ear stoppers for infected ears, skull covers-post brain surgery, antimicrobial elastic adhesive closures (instead of sutures), and the like.

Although the present invention has been described in relation to a particular embodiment thereof, many other variations and other uses will become apparent to those skilled in the art. It is preferred, therefore, that the present invention be limited not by the specific disclosure herein, but only by the appended claims.

What is claimed is:

1. An antimicrobial sponge material composition having a visual indication of an antimicrobial activity comprising a hydroxylated acetalized polyvinyl alcohol complexed with iodine and plastisized with a polyol, said sponge material composition having a yellow or gold colored surface and being capable of both releasing free iodine from the surface and changing surface color from a yellow or gold color to a black color upon surface contact with an aqueous fluid, thereby providing a visual indication that the antimicrobial activity of the sponge material composition has been activated by releasing free iodine.

2. The antimicrobial sponge material composition as defined in claim 1 wherein the polyol is selected from the group consisting of ethylene glycol, propylene glycol, diethylene glycol, triethylene glycol, dipropylene glycol, tripropylene glycol, neopentyl glycol, glycerin, trimethylol propane, trimethylol ethane and mixtures thereof.

3. The antimicrobial sponge material composition as defined in claim 1 wherein the polyol is triethylene glycol.

4. The antimicrobial sponge material composition as defined in claim 1 wherein the aqueous fluid is water, blood, serum, plasma, sputum or other bodily fluids.

5. The antimicrobial sponge material composition as defined in claim 1 wherein the black color disappears as the iodine component of the complex is depleted and complete iodine depletion is indicated by the color of the surface of the sponge material changing to a white color, thereby providing a visual indication that the antimicrobial activity of the sponge material has been depleted.

6. A method for making a hydroxylated acetalized polyvinyl alcohol sponge material complexed with iodine and having antimicrobial activity comprising: applying a polyol to a surface of said complex thereby forming iodates and iodine dioxide on the surface of the iodine/acetalized polyvinyl alcohol complex and providing a plastisized yellow or gold colored surface of the sponge being capable of both releasing free iodine from the surface and changing surface color from a yellow or gold color to a black color upon surface contact with an aqueous fluid, thereby providing a visual indication that the antimicrobial activity of the sponge composition has been activated by releasing free iodine.

7. The method of claim 6 wherein said applying step is immersing the sponge material in a bath containing the polyol.

8. The method of claim 6 wherein said polyol is selected from the group consisting of ethylene glycol, propylene glycol, diethylene glycol, triethylene glycol, dipropylene glycol, tripropylene glycol, neopentyl glycol, glycerin, trimethylol propane, trimethylol ethane and mixtures thereof.

9. The method of claim 6 wherein the polyol is triethylene glycol.

10. The method of claim 6 wherein said applying step is spraying or rolling the polyol on the surface of the sponge material.

11. An antimicrobial sponge made by a method comprising:

providing a black hydroxylated polyvinyl acetal sponge formed of a composition comprising acetalized polyvinyl alcohol complexed with iodine; wherein said composition is capable of releasing free iodine in the presence of water; and, contacting at least the outer surfaces of said sponge with a polyol selected for both (a) plasticizing at least said outer surfaces; and, (b) causing said at least said outer surfaces to become yellow to gold in color and become black again only when contacted with an aqueous fluid.

12. A method of making an antimicrobial sponge comprising:

providing a black hydroxylated polyvinyl acetal sponge formed of a composition comprising acetalized polyvinyl alcohol complexed with iodine; wherein said composition is capable of releasing free iodine in the presence of water; and, contacting at least the outer surfaces of said sponge with a polyol selected for both (a) plasticizing at least said outer surfaces; and, (b) causing said at least said outer surfaces to become yellow to gold in color and become black again only when contacted with an aqueous fluid.

* * * * *